United States Patent
Kirsch et al.

(10) Patent No.: US 6,632,838 B1
(45) Date of Patent: Oct. 14, 2003

(54) USE OF BISSULFONAMIDES FOR PRODUCING MEDICINES FOR THE TREATMENT OF HYPERLIPIDEMIA

(75) Inventors: Reinhard Kirsch, Braunschweig (DE); Hans-Ludwig Schaefer, Hochheim (DE); Eugen Falk, Frankfurt (DE); Norbert Krass, Hofheim (DE)

(73) Assignee: Aventis Pharma Deutschland GmbH, Frankfrut am Main (DE)

( * ) Notice: Subject to any disclaimer, the term of this patent is extended or adjusted under 35 U.S.C. 154(b) by 0 days.

(21) Appl. No.: 09/653,253

(22) Filed: Aug. 31, 2000

(30) Foreign Application Priority Data

Sep. 1, 1999 (DE) .......................... 199 41 559

(51) Int. Cl.[7] ..................... A61K 31/18; A61K 31/495; A61K 31/50; A61K 31/445
(52) U.S. Cl. ................ 514/602; 514/603; 514/601; 514/252.11; 514/252.12; 514/331; 514/326
(58) Field of Search .............. 514/252.11, 602, 514/603, 601, 252.12, 331, 326

(56) References Cited

U.S. PATENT DOCUMENTS

| 3,876,632 A | * | 4/1975 | Sturm et al. |
| 4,849,444 A |   | 7/1989 | Lang et al. |
| 5,143,937 A |   | 9/1992 | Lang et al. |

FOREIGN PATENT DOCUMENTS

| EP | 0 081 425 A1 | 6/1983 |
| EP | 0 288 028 A2 | 10/1988 |
| EP | 0 384 279 A1 | 8/1990 |
| FR | 2294705 | * 7/1976 |

OTHER PUBLICATIONS

Lygth et al. Ed., The Merck Manual, 11th ed., pp. 212–216 (1966).*
International Search Report for International Application No. PCT/EP 00/08026 (Nov. 29, 2001). *report lists the above references*.
International Search Report for International Application No. PCT/EP 00/08026 (Nov. 29, 2001).

* cited by examiner

Primary Examiner—Sreeni Padmanabhan
Assistant Examiner—S. Jiang
(74) Attorney, Agent, or Firm—Finnegan, Henderson, Farabow, Garrett & Dunner, LLP

(57) ABSTRACT

The use of bissulfonamides for producing medicines for the treatment of hyperlipidemia.

The invention relates to the use of bissulfonamides and their salts for producing medicines for the treatment of hyperlipidemia.

The use of compounds of formula I

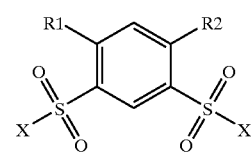

I in which the radicals have the stated meanings, and of their salts for producing a medicine for the treatment of hyperlipidemia is described.

8 Claims, No Drawings

USE OF BISSULFONAMIDES FOR PRODUCING MEDICINES FOR THE TREATMENT OF HYPERLIPIDEMIA

The invention relates to the use of bissulfonamides and their physiologically tolerated salts and physiologically functional derivatives for producing medicines for the prevention and treatment of hyperlipidemia and arteriosclerotic disorders.

U.S. Pat. No. 3,876,632 describes bissulfonamides as antihypertensives.

The invention was based on the object of providing compounds which display a therapeutically utilizable hypolipidemic effect.

The invention therefore relates to the use of compounds of formula I

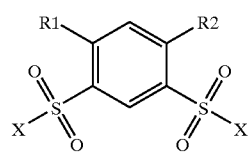

in which:

X, R1, and R2 are, independently of one another, NR6R7, pyrrolidinyl, piperidinyl, piperazinyl, morpholinyl, or tetrahydropyridinyl, in which each ring is optionally substituted independently of one another by phenyl, $(C_1-C_6)$-alkyl-phenyl, $(C_1-C_6)$-alkyl, $(C_1-C_6)$-alkyl-OH, O-phenyl, S-phenyl, (CO)—$(C_1-C_6)$-alkyl, or (CO)-phenyl, where the phenyl substituent is unsubstituted or mono- or disubstituted independently of one another by F, Cl, Br, OH, $CF_3$, CN, $OCF_3$, O—$(C_1-C_6)$-alkyl, S—$(C_1-C_6)$-alkyl, SO—$(C_1-C_6)$-alkyl, $SO_2$—$(C_1-C_6)$-alkyl, $(C_1-C_6)$-alkyl, $(C_3-C_6)$-cycloalkyl, COOH, COO$(C_1-C_6)$alkyl, COO$(C_3-C_6)$ cycloalkyl, $CONH_2$, CONH$(C_1-C_6)$alkyl, CON$[(C_1-C_6)$alkyl$]_2$, CONH$(C_3-C_6)$cycloalkyl, $NH_2$, NH—CO—$(C_1-C_6)$-alkyl, or NH—CO-phenyl;

R6 and R7 are, independently of one another, H, $(C_1-C_6)$-alkyl, $(C_1-C_6)$-alkyl-O—$(C_1-C_6)$-alkyl, O—$(C_1-C_6)$-alkyl, $(C_3-C_6)$-cycloalkyl, CO—$(C_1-C_6)$-alkyl, $(C_1-C_6)$-alkyl-NH—C(O)—$(C_1-C_6)$-alkyl, $(C_1-C_6)$-alkyl-NH—$(C_1-C_6)$-alkyl, $(C_1-C_6)$-alkyl-N—$[(C_1-C_6)$-alkyl$]_2$, $(C_1-C_6)$-alkyl-O-phenyl, CHO, CO-phenyl, or $(CH_2)_n$—Ar, where n is optionally the integer 0, 1, 2, 3, 4, 5, or 6, and Ar is chosen from phenyl, biphenylyl, 1- or 2-naphthyl, 1- or 2-tetrahydrofuranyl, 2-, 3-, or 4-pyridyl, 2- or 3-thienyl, 2- or 3-furyl, 2-, 4-, or 5-thiazolyl, 2-, 4-, or 5-oxazolyl, 1-pyrazolyl, 3-, 4-, or 5-isoxazolyl, $(C_3-C_6)$-cycloalkyl, piperidinyl, pyrrolidinyl, 2- or 3-pyrrolyl, 2- or 3-pyridazinyl, 2-, 4-, or 5-pyrimidinyl, 2-pyrazinyl, 2-(1,3,5-triazinyl), 2-, 3-, or 4-morpholinyl, 2- or 5-benzimidazolyl, 2-benzothiazolyl, 1,2,4-triazol-3-yl, 1,2,4-triazol-5-yl, tetrazol-5-yl, indol-3-yl, indol-5-yl, or N-methyl-imidazol-2-, -4-, or -5-yl, and Ar is optionally mono- or disubstituted independently of one another by F, Cl, Br, OH, $CF_3$, $NO_2$, CN, $OCF_3$, O—$CH_2$—O, O—$(C_1-C_6)$-alkyl, S—$(C_1-C_6)$-alkyl, SO—$(C_1-C_6)$-alkyl, $SO_2$—$(C_1-C_6)$-alkyl, $(C_1-C_6)$-alkyl, $(C_3-C_6)$-cycloalkyl, COOH, COO$(C_1-C_6)$alkyl, COO$(C_3-C_6)$cycloalkyl, $CONH_2$, CONH$(C_1-C_6)$alkyl, CON$[(C_1-C_6)$alkyl$]_2$, CONH$(C_3-C_6)$cycloalkyl, $NH_2$, NH—CO—$(C_1-C_6)$-alkyl, NH—CO-phenyl, pyrrolidin-1-yl, morpholin-1-yl, piperidin-1-yl, piperazin-1-yl, 4-methyl-piperazin-1-yl, $(CH_2)_n$-phenyl, O—$(CH_2)_n$-phenyl, S—$(CH_2)_n$-phenyl, or $SO_2$—$(CH_2)_n$-phenyl, where n is the integer 0, 1, 2, or 3;

or a physiologically tolerated salt or a physiologically functional derivative thereof for producing a medicine for the prevention and treatment of hyperlipidemia.

It is preferred to use compounds of formula I in which one or more radical(s) has or have the following meaning:

R1 is NR6R7, pyrrolidinyl, piperidinyl, piperazinyl, or tetrahydropyridinyl, in which each ring is optionally substituted independently of one another by phenyl, $(C_1-C_6)$-alkyl-phenyl, $(C_1-C_6)$-alkyl, $(C_1-C_6)$-alkyl-OH, O-phenyl, S-phenyl, (CO)—$(C_1-C_6)$-alkyl, or (CO)-phenyl, where the phenyl substituent is unsubstituted or mono- or disubstituted independently of one another by F, Cl, Br, $CF_3$, CN, $OCF_3$, O—$(C_1-C_6)$-alkyl, S—$(C_1-C_6)$-alkyl, $(C_1-C_6)$-alkyl, $(C_3-C_6)$-cycloalkyl, COOH, COO$(C_1-C_6)$-alkyl, COO$(C_3-C_6)$ cycloalkyl, $CONH_2$, CONH$(C_1-C_6)$alkyl, CON$[(C_1-C_6)$alkyl$]_2$, $NH_2$, NH—CO—$(C_1-C_6)$-alkyl, or NH—CO-phenyl;

R6 and R7 are, independently of one another, H, $(C_1-C_6)$-alkyl, $(C_1-C_6)$-alkyl-O—$(C_1-C_6)$-alkyl, $(C_3-C_6)$-cycloalkyl, CO—$(C_1-C_6)$-alkyl, $(C_1-C_6)$-alkyl-NH—C(O)—$(C_1-C_6)$-alkyl, $(C_1-C_6)$-alkyl-NH—$(C_1-C_6)$-alkyl, $(C_1-C_6)$-alkyl-N—$[(C_1-C_6)$-alkyl$]_2$, or $(CH_2)_n$—Ar, where n is optionally the integer 0,1, 2, 3, 4, 5, or 6, and Ar is chosen from phenyl, biphenylyl, 1- or 2-naphthyl, 2-, 3-, or 4-pyridyl, 2- or 3-thienyl, 2-, 4-, or 5-thiazolyl, 2-, 4-, or 5-oxazolyl, 3- or 5-isoxazolyl, $(C_3-C_6)$-cycloalkyl, piperidinyl, pyrrolidinyl, 2-, 4-, or 5-pyrimidinyl, 2-, 3-, or 4-morpholinyl, 2- or 5-benzimidazolyl, 2-benzothiazolyl, indol-3-yl, or indol-5-yl, and Ar is optionally mono- or disubstituted independently of one another by F. Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $SO_2$—$(C_1-C_6)$-alkyl, $(C_1-C_6)$-alkyl, $(C_3-C_6)$-cycloalkyl, COOH, COO$(C_1-C_6)$alkyl, COO$(C_3-C_6)$cycloalkyl, $CONH_2$, CONH$(C_1-C_6)$alkyl, $NH_2$, NH—CO-phenyl, $(CH_2)_n$-phenyl, O—$(CH_2)_n$-phenyl, or S—$(CH_2)_n$-phenyl, where n is the integer 0, 1, 2, or 3;

R2 is NR8R9 or piperazinyl, in which piperazinyl is optionally substituted independently of one another by $(C_1-C_6)$-alkyl-phenyl, $(C_1-C_6)$-alkyl, $(C_1-C_6)$-alkyl-OH, O-phenyl, S-phenyl, (CO)—$(C_1-C_6)$-alkyl, or (CO)-phenyl;

R8 and R9 are, independently of one another, H, $(C_1-C_6)$-alkyl, $(C_3-C_6)$-cycloalkyl, CO—$(C_1-C_6)$-alkyl, $(C_1-C_6)$-alkyl-NH—$(C_1-C_6)$-alkyl, $(C_1-C_6)$-alkyl-N—$[(C_1-C_6)$-alkyl$]_2$, or $(CH_2)_n$—Ar, where n is the integer 0, 1, 2, 3, 4, 5, or 6, and Ar is chosen from phenyl, 2-, 3-, or 4-pyridyl, piperidinyl, pyrrolidinyl, or morpholinyl;

X is NR10R11, pyrrolidinyl, piperidinyl, piperazinyl, or morpholinyl, in which each ring is optionally substituted independently of one another by phenyl, $(C_1-C_6)$ alkyl-phenyl, $(C_1-C_6)$-alkyl, $(C_1-C_6)$-alkyl-OH, O-phenyl, S-phenyl, (CO)—$(C_1-C_6)$-alkyl, or (CO)-phenyl, where the phenyl substituent is unsubstituted or mono- or disubstituted independently of one another by F, Cl, Br, $CF_3$, CN, $OCF_3$, O—$(C_1-C_6)$-alkyl, $(C_1-C_6)$-alkyl, $(C_3-C_6)$-cycloalkyl, COOH, COO$(C_1-C_6)$-alkyl, COO$(C_3-C_6)$cycloalkyl, $CONH_2$, CONH$(C_1-C_6)$ alkyl, CON$[(C_1-C_6)$alkyl$]_2$, $NH_2$, NH—CO—$(C_1-C_6)$-alkyl, or NH—CO-phenyl;

R10 and R11 are, independently of one another, H, $(C_1-C_6)$-alkyl, $(C_1-C_6)$-alkyl-O—$(C_1-C_6)$-alkyl, $(C_3-C_6)$-cycloalkyl, CO—$(C_1-C_6)$-alkyl, $(C_1-C_6)$-alkyl-NH—$(C_1-C_6)$-alkyl, $(C_1-C_6)$-alkyl-N—$[(C_1-C_6)$-alkyl$]_2$, CO-phenyl, or $(CH_2)_n$—Ar, where n is the integer 0, 1, 2, 3, 4, 5, or 6, and Ar is chosen from phenyl, biphenylyl, 1- or 2-naphthyl, 1- or 2-tetrahydrofuranyl, 2-, 3-, or 4-pyridyl, 2- or 3-thienyl, 2- or 3-furyl, 2-, 4-, or 5-thiazolyl, 2-, 4-, or 5-oxazolyl, 3- or 5-isoxazolyl, piperidinyl, pyrrolidinyl, 2-, 4-, or 5-pyrimidinyl, 2-, 3-, or 4-morpholinyl, or 2-benzothiazolyl, and Ar is optionally mono- or disubstituted independently of one another by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $SO_2$—$(C_1-C_6)$-alkyl, $(C_1-C_6)$-alkyl, $(C_3-C_6)$-cycloalkyl, $CONH_2$, CONH$(C_1-C_6)$alkyl, CON$[(C_1-C_6)$alkyl$]_2$, NH—CO—$(C_1-C_6)$-alkyl, NH—CO-phenyl, or $(CH_2)_n$-phenyl where n is the integer 0, 1, 2, or 3;

or a physiologically tolerated salt or a physiologically functional derivative thereof for producing a medicine for the prevention and treatment of hyperlipidemia.

It is particularly preferred to use compounds of formula I in which one or more radical(s) has or have the following meaning:

R1 is NR6R7, piperidinyl, piperazinyl, or tetrahydropyridinyl, in which each ring is optionally substituted independently of one another by phenyl or $(C_1-C_6)$-alkyl-phenyl;

R6 and R7 are, independently of one another, H, $(C_1-C_6)$-alkyl, $(C_1-C_6)$-alkyl-O—$(C_1-C_6)$-alkyl, $(C_3-C_6)$-cycloalkyl, $(C_1-C_6)$-alkyl-NH—C(O)—$(C_1-C_6)$-alkyl, $(C_1-C_6)$-alkyl-NH—$(C_1-C_6)$-alkyl, $(C_1-C_6)$-alkyl-N—$[(C_1-C_6)$-alkyl$]_2$, or $(CH_2)_n$—Ar, where n is the integer 0, 1, 2, 3, 4, 5, or 6, and Ar is chosen from phenyl, 1- or 2-naphthyl, 2-, 3-, or 4-pyridyl, $(C_3-C_6)$-cycloalkyl, piperidinyl, pyrrolidinyl, 2-, 4-, or 5-pyrimidinyl, or 2-, 3-, or 4-morpholinyl, and Ar is optionally mono- or disubstituted independently of one another by F, Cl, Br, OH, $CF_3$, $NO_2$, CN, $OCF_3$, O—$(C_1-C_6)$-alkyl, $(C_1-C_6)$-alkyl, or $NH_2$;

R2 is NR8R9 or piperazinyl, in which piperazinyl is optionally substituted by $(C_1-C_6)$-alkyl;

R8 and R9 are, independently of one another, H, $(C_1-C_6)$-alkyl, $(C_3-C_6)$-cycloalkyl, CO—$(C_1-C_6)$-alkyl, $(C_1-C_6)$-alkyl-NH—$(C_1-C_6)$-alkyl, $(C_1-C_6)$-alkyl-N—$[(C_1-C_6)$-alkyl$]_2$, or $(CH_2)_n$—Ar, where n is the integer 0, 1, 2, 3, 4, 5, or 6, and Ar is chosen from phenyl, 2-, 3-, or 4-pyridyl, piperidinyl, pyrrolidinyl, or morpholinyl;

X is NR10R11, pyrrolidinyl, piperidinyl, or morpholinyl, in which each ring is optionally substituted independently of one another by phenyl or $(C_1-C_6)$-alkyl-phenyl;

R10 and R11 are, independently of one another, H, $(C_1-C_6)$-alkyl, $(C_1-C_6)$-alkyl-O—$(C_1-C_6)$-alkyl, $(C_3-C_6)$-cycloalkyl, $(C_1-C_6)$-alkyl-NH—$(C_1-C_6)$-alkyl, $(C_1-C_6)$-alkyl-N—$[(C_1-C_6)$-alkyl$]_2$, $(CH_2)_n$—Ar, where n is the integer 0, 1, 2, 3, 4, 5, or 6, and Ar is chosen from phenyl or 2- or 3-thienyl;

or a physiologically tolerated salt thereof for producing a medicine for the prevention and treatment of hyperlipidemia.

The invention relates to the use of compounds of formula I in the form of their racemates, racemic mixtures, and pure enantiomers, and to their diastereomers and mixtures thereof.

The alkyl, alkenyl, and alkynyl radicals in the substituents X, R1, and R2 may be either straight-chain or branched.

The term "substituted" means mono- or polysubstitution unless otherwise indicated.

Pharmaceutically acceptable salts are particularly suitable for medical applications because their solubility in water is higher than the initial or basic compounds. These salts must have a pharmaceutically acceptable anion or cation. Suitable pharmaceutically acceptable acid addition salts of compounds of formula I are salts of inorganic acids such as hydrochloric, hydrobromic, phosphoric, metaphosphoric, nitric, sulfamic, and sulfuric acids, and organic acids such as, for example, acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric, and trifluoroacetic acids. The chloride salt and the tartaric acid salt are particularly preferably used for medical purposes. Suitable pharmaceutically acceptable basic salts are ammonium salts, alkali metal salts (such as sodium and potassium salts), and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in nontherapeutic, for example, in vitro, applications.

The term "physiologically functional derivative" used herein refers to any physiologically tolerated derivative of a compound according to the invention, for example, an ester, which is able on administration to a mammal such as, for example, a human, to form (directly or indirectly) such a compound or an active metabolite thereof.

A further aspect of this invention is the use of prodrugs of compounds of formula I. Such prodrugs can be metabolized in vivo to a compound of formula I. These prodrugs may themselves be active or not.

Compounds of formula I may also exist in various polymorphous forms, for example, as amorphous and crystalline polymorphous forms. All polymorphous forms of compounds of formula I lie within the scope of the invention and are a further aspect of the invention.

All references hereinafter to "compound(s) of formula I" refer to compound(s) of formula I as described above, or the salts, solvates, or physiologically functional derivatives thereof as described herein.

The amount of a compound of formula I which is necessary to achieve the desired biological effect depends on a number of factors, for example, the specific compound chosen, the intended use, the mode of administration, and the clinical condition of the patient. In general, the daily dose is in the range from 0.3 mg to 100 mg (typically from 3 mg to 50 mg) per day and per kilogram of body weight, for example, 3 to 10 mg/kg/day. An intravenous dose may be, for example, in the range from 0.3 mg/kg to 1 mg/kg, which can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. It is thus possible for ampoules for injections to contain, for example, from 1 mg to 100 mg, and single-dose formulations which can be administered orally, such as, for example, tablets or capsules, to contain, for example, from 1 mg to 1000 mg, typically from 10 mg to 600 mg. In the case of pharmaceutically acceptable salts, the aforementioned weight data are based on the weight of the salt of the compound of formula I. For the prophylaxis or therapy of the abovementioned conditions, compounds of formula I can be used as the compound itself, but they are preferably in the form of a pharmaceutical composition with an acceptable carrier. The carrier must, of course, be acceptable in the sense that it is compatible with the other ingredients of the composition and is not hazardous for the patient's health. The carrier may be a solid or a liquid or both, and is preferably formulated with the compound as single dose, for example, as tablet, which may contain from 0.05% to 95% by weight of the active ingredient. Further pharmaceutically active substances may likewise be present, including other compounds of formula I. The pharmaceutical compositions according to the invention can be produced by one of the known pharmaceutical methods which essentially consist of mixing the ingredients with pharmacologically acceptable carriers and/or excipients.

Pharmaceutical compositions according to the invention are those suitable for oral, rectal, topical, peroral (for example sublingual), and parenteral (for example, subcutaneous, intramuscular, intradermal, or intravenous) administration, although the most suitable mode of administration in each individual case depends on the nature and severity of the condition to be treated and on the nature of the compound of formula I used in each case. Coated formulations and coated slow-release formulations also lie within the scope of the invention. Formulations resistant to acid and gastric fluid are preferred. Suitable coatings resistant to gastric fluid comprise cellulose acetate phthalate, polyvinyl acetate, hydroxypropylmethylcellulose phthalate, and anionic polymers of methacrylic acid and methyl methacrylate.

Suitable pharmaceutical compounds for oral administration may be in the form of separate units such as, for example, capsules, cachets, suckable tablets, or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tabletting the compound in free-flowing form, such as, for example, a powder or granules, where appropriate mixed with a binder, lubricant, inert diluent, and/or a (plurality of) surface-active/dispersing agent(s) in a suitable machine. Molded tablets can be produced by molding the compound which is in powder form and is moistened with an inert liquid diluent in a suitable machine.

Pharmaceutical compositions suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Suitable pharmaceutical compositions for parenteral administration comprise preferably sterile aqueous preparations of a compound of formula I, which are preferably isotonic with the blood of the intended recipient. These preparations are preferably administered intravenously, although administration may also take place by subcutaneous, intramuscular, or intradermal injection. These preparations can preferably be produced by mixing the compound with water and making the resulting solution sterile and isotonic with blood. Injectable compositions according to the invention generally contain from about 0.1% to about 5% by weight of the active compound.

Suitable pharmaceutical compositions for rectal administration are preferably in the form of single-dose suppositories. These can be produced by mixing a compound of formula I with one or more conventional solid carriers, for example cocoa butter, and shaping the resulting mixture.

Suitable pharmaceutical compositions for topical application to the skin are preferably in the form of ointment, cream, lotion, paste, spray, aerosol, or oil. Carriers which can be used are petrolatum, lanolin, polyethylene glycols, alcohols, and combinations of two or more of these substances. The active ingredient is generally present in a concentration of from about 0.1% to about 15% by weight of the composition, for example from about 0.5% to about 2%.

Transdermal administration is also possible. Suitable pharmaceutical compositions for transdermal uses can be in the form of single plasters which are suitable for long-term close contact with the patient's epidermis. Such plasters suitably contain the active ingredient in an optionally buffered aqueous solution, dissolved and/or dispersed in an adhesive, or dispersed in a polymer. A suitable active ingredient concentration is about 1% to about 35%, preferably about 3% to about 15%. As a special possibility, the active ingredient can be released as described, for example, in *Pharmaceutical Research*, 2(6) (1986) 318, by electrotransport or iontophoresis.

The following preparations serve to illustrate the invention without restricting it, however.

EXAMPLE A

Soft gelatin capsules containing 100 mg of active ingredient per capsule:

|  | per capsule |
|---|---|
| Active ingredient | 100 mg |
| Triglyceride mixture fractionated from coconut fat | 400 mg |
|  | 500 mg |

EXAMPLE B

Emulsion containing 60 mg of active ingredient per 5 ml:

|  | per 100 ml emulsion |
|---|---|
| Active ingredient | 1.2 g |
| Neutral oil | q.s. |
| Sodium carboxymethylcellulose | 0.6 g |

|                              | per 100 ml emulsion |
|------------------------------|---------------------|
| Polyoxyethylene stearate     | q.s.                |
| Glycerol, pure               | 0.2 g to 2.0 g      |
| Flavoring                    | q.s.                |
| Water (deionized or distilled)| ad 100 ml          |

EXAMPLE C

Rectal pharmaceutical form containing 40 mg of active ingredient per suppository:

|                 | per suppository |
|-----------------|-----------------|
| Active ingredient | 40 mg         |
| Suppository base  | ad 2 g        |

EXAMPLE D

Tablets containing 40 mg of active ingredient per tablet:

|                    | per tablet |
|--------------------|------------|
| Active ingredient  | 40 mg      |
| Lactose            | 600 mg     |
| Corn starch        | 300 mg     |
| Soluble starch     | 20 mg      |
| Magnesium stearate | 40 mg      |
|                    | 1000 mg    |

EXAMPLE E

Coated tablets containing 50 mg of active ingredient per coated tablet:

|                       | per coated tablet |
|-----------------------|-------------------|
| Active ingredient     | 50 mg             |
| Corn starch           | 100 mg            |
| Lactose               | 60 mg             |
| Sec. calcium phosphate| 30 mg             |
| Soluble starch        | 5 mg              |
| Magnesium stearate    | 10 mg             |
| Colloidal silica      | 5 mg              |
|                       | 260 mg            |

EXAMPLE F

The following formulas are suitable for producing the contents of hard gelatin capsules:

| a) | Active ingredient | 100 mg |
|----|-------------------|--------|
|    | Corn starch       | 300 mg |
|    |                   | 400 mg |

| b) | Active ingredient | 140 mg |
|----|-------------------|--------|
|    | Lactose           | 180 mg |
|    | Corn starch       | 180 mg |
|    |                   | 500 mg |

EXAMPLE G

Drops can be produced in accordance with the following formula (100 mg of active ingredient in 1 ml=20 drops):

| Active ingredient  | 10 g      |
| Methyl benzoate    | 0.07 g    |
| Ethyl benzoate     | 0.03 g    |
| Ethanol 96% pure   | 5 ml      |
| Demineralized water| ad 100 ml |

The invention also relates to a process for preparing compounds of formula I, comprising preparing compounds of formula I as shown in the following reaction diagram:

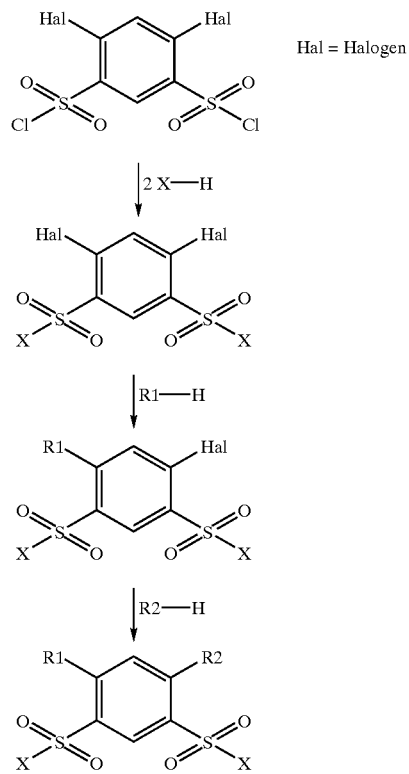

The term "halogen" means fluorine, chlorine, bromine, or iodine.

The examples detailed below served to illustrate the invention without restricting it, however. The stated decomposition points are not corrected and generally depend on the heating rate.

TABLE 1

Example I

| Ex. | R1 | R2 | X | Molecular formula | MW | MS (M + H⁺) | Mp (° C.) |
|---|---|---|---|---|---|---|---|
| 1 | 4-N(CH$_3$)-piperazin-1-yl | 4-N(CH$_3$)-piperazin-1-yl | NH-cyclohexyl | C$_{28}$H$_{48}$N$_6$O$_4$S$_2$ | 596.9 | 597.3 | 232.5 |
| 2 | NH-benzyl | 4-N(CH$_3$)-piperazin-1-yl | NH-cyclohexyl | C$_{30}$H$_{45}$N$_5$O$_4$S$_2$ | 603.8 | 604.3 | 194 |
| 3 | 4-N(CH$_3$)-piperazin-1-yl | 4-N(CH$_3$)-piperazin-1-yl | N(CH$_3$)-benzyl | C$_{32}$H$_{44}$N$_6$O$_4$S$_2$ | 640.9 | 641.3 | 124 |
| 4 | NH-benzyl | 4-N(CH$_3$)-piperazin-1-yl | NH-phenyl | C$_{30}$H$_{33}$N$_5$O$_4$S$_2$ | 591.8 | 592.3 | 211 |
| 5 | NH-benzyl | 4-N(CH$_3$)-piperazin-1-yl | pyrrolidin-1-yl | C$_{26}$H$_{37}$N$_5$O$_4$S$_2$ | 547.7 | 548.3 | 173 |
| 6 | 4-N(CH$_3$)-piperazin-1-yl | 4-N(CH$_3$)-piperazin-1-yl | NH-phenyl | C$_{30}$H$_{40}$N$_6$O$_4$S$_2$ | 612.8 | 613.3 | 189 |
| 7 | 4-N(CH$_3$)-piperazin-1-yl | 4-N(CH$_3$)-piperazin-1-yl | N(CH$_3$)-phenyl | C$_{30}$H$_{40}$N$_6$O$_4$S$_2$ | 612.8 | 613.3 | 175 |
| 8 | 4-N(CH$_3$)-piperazin-1-yl | 4-N(CH$_3$)-piperazin-1-yl | piperidin-1-yl | C$_{26}$H$_{44}$N$_6$O$_4$S$_2$ | 568.8 | 569.3 | 202.5 |
| 9 | NH-benzyl | 4-N(CH$_3$)-piperazin-1-yl | N(CH$_3$)-phenyl | C$_{32}$H$_{37}$N$_5$O$_4$S$_2$ | 619.8 | 620.2 | 149 |
| 10 | NH—CH$_2$-pyrid-2-yl | 4-N(CH$_3$)-piperazin-1-yl | N(CH$_3$)-phenyl | C$_{31}$H$_{36}$N$_6$O$_4$S$_2$ | 620.8 | 621.3 | 155.5 |
| 11 | NH—CH$_2$-(3,4-methylenedioxyphenyl) | 4-N(CH$_3$)-piperazin-1-yl | pyrrolidin-1-yl | C$_{27}$H$_{37}$N$_5$O$_6$S$_2$ | 591.8 | 591.3 | 118 (decomp.) |
| 12 | NH-benzyl | 4-N(CH$_3$)-piperazin-1-yl | NH—CH$_2$—CH(CH$_3$)$_2$ | C$_{26}$H$_{41}$N$_5$O$_4$S$_2$ | 551.8 | 552.3 | 169 |
| 13 | NH—CH$_2$-cyclohexyl | 4-N(CH$_3$)-piperazin-1-yl | morpholin-4-yl | C$_{26}$H$_{43}$N$_5$O$_6$S$_2$ | 585.8 | 586.3 | 249 |
| 14 | NH—CH$_2$-tetrahydrofuran-2-yl | 4-N(CH$_3$)-piperazin-1-yl | N(CH$_3$)-phenyl | C$_{30}$H$_{39}$N$_5$O$_5$S$_2$ | 613.8 | 614.3 | 147.5 |
| 15 | NH-propyl-phenyl | 4-N(CH$_3$)-piperazin-1-yl | morpholin-4-yl | C$_{28}$H$_{41}$N$_5$O$_6$S$_2$ | 607.8 | 608.3 | 167 |
| 16 | NH-benzyl | 4-N(CH$_3$)-piperazin-1-yl | N(ethyl)$_2$ | C$_{26}$H$_{41}$N$_5$O$_4$S$_2$ | 551.8 | | 89 |
| 17 | NH-propyl-phenyl | 4-N(CH$_3$)-piperazin-1-yl | piperidin-1-yl | C$_{30}$H$_{45}$N$_5$O$_4$ | 603.8 | | 134 |
| 18 | NH-propyl-phenyl | 4-N(CH$_3$)-piperazin-1-yl | NH-benzyl | C$_{34}$H$_{41}$N$_5$O$_4$S$_2$ | 647.9 | | 152 |
| 19 | NH—CH$_2$-cyclohexyl | 4-N(CH$_3$)-piperazin-1-yl | N(ethyl)$_2$ | C$_{26}$H$_{47}$N$_5$O$_4$ | 557.8 | | 109 |
| 20 | NH-propyl-phenyl | 4-N(CH$_3$)-piperazin-1-yl | N(ethyl)$_2$ | S$_2$C$_{28}$H$_{45}$N$_5$O$_4$S$_2$ | 579.8 | 580.3 | Oil |
| 21 | NH-ethyl-phenyl | 4-N(CH$_3$)-piperazin-1-yl | piperidin-1-yl | C$_{29}$H$_{43}$N$_5$O$_4$S$_2$ | 589.8 | 590.3 | 70 |
| 22 | NH-ethyl-phenyl | 4-N(CH$_3$)-piperazin-1-yl | N(ethyl)$_2$ | C$_{27}$H$_{43}$N$_5$O$_4$S$_2$ | 565.8 | | Oil |
| 23 | NH-ethyl-phenyl | 4-N(CH$_3$)-piperazin-1-yl | N(CH$_3$)-phenyl | C$_{33}$H$_{39}$N$_5$O$_4$S$_2$ | 633.8 | 634.3 | 168 |
| 24 | NH—CH$_2$-cyclohexyl | 4-N(CH$_3$)-piperazin-1-yl | N(CH$_3$)-phenyl | C$_{32}$H$_{43}$N$_5$O$_4$S$_2$ | 625.9 | | 174 |
| 25 | NH-propyl-phenyl | 4-N(CH$_3$)-piperazin-1-yl | N(CH$_3$)-phenyl | C$_{34}$H$_{41}$N$_5$O$_4$S$_2$ | 647.9 | | 132 |
| 26 | NH-propyl-phenyl | 4-N(CH$_3$)-piperazin-1-yl | Pyrrolidin-1-yl | C$_{28}$H$_{41}$N$_5$O$_4$S$_2$ | 575.8 | | 160 |
| 27 | NH-propyl-phenyl | 4-N(CH$_3$)-piperazin-1-yl | N(CH$_3$)-benzyl | C$_{36}$H$_{45}$N$_5$O$_4$S$_2$ | 675.9 | | 113 |
| 28 | NH-ethyl-phenyl | 4-N(CH$_3$)-piperazin-1-yl | N-morpholinyl | C$_{27}$H$_{39}$N$_5$O$_6$S$_2$ | 593.8 | 594.3 | 181 |
| 29 | NH-ethyl-N-(Et)$_2$ | 4-N(CH$_3$)-piperazin-1-yl | NH—CH$_2$—CH(CH$_3$)$_2$ | C$_{25}$H$_{47}$N$_5$O$_4$S$_2$ | 560.8 | 561.3 | 158 |
| 30 | NH—CH$_2$-pyrid-3-yl | NH-ethyl-N(CH$_3$)$_2$ | N(CH$_3$)-benzyl | C$_{32}$H$_{40}$N$_6$O$_4$S$_2$ | 636.8 | 637.3 | |
| 31 | NH-ethyl-N(ethyl)$_2$ | NH-ethyl-N(CH$_3$)$_2$ | N(CH$_3$)-benzyl | C$_{32}$H$_{48}$N$_6$O$_4$S$_2$ | 644.9 | 645.3 | |
| 32 | NH-propyl-O—CH$_3$ | NH-ethyl-N(CH$_3$)$_2$ | N(CH$_3$)-benzyl | C$_{30}$H$_{43}$N$_5$O$_5$S$_2$ | 617.8 | 618.3 | |
| 33 | NH-ethyl-N-morpholin-4-yl | NH-ethyl-N-pyrrolidin-1-yl | N(CH$_3$)-benzyl | C$_{34}$H$_{48}$N$_6$O$_5$S$_2$ | 684.9 | 685.3 | |
| 34 | NH-ethyl-N-pyrrolidin-1-yl | NH-ethyl-NH-acetyl | N(CH$_3$)-benzyl | C$_{32}$H$_{44}$N$_6$O$_5$S$_2$ | 656.9 | 657.3 | |
| 35 | NH-propyl-O—CH$_3$ | NH-ethyl-N-pyrrolidin-1-yl | N(CH$_3$)-benzyl | C$_{32}$H$_{45}$N$_5$O$_5$S$_2$ | 643.9 | 644.3 | |
| 36 | N-piperidinyl | N(ethyl)-ethyl-N(CH$_3$)$_2$ | N(CH$_3$)-benzyl | C$_{33}$H$_{47}$N$_5$O$_4$S$_2$ | 641.9 | 642.3 | |
| 37 | NH-ethyl-N-morpholin-4-yl | NH-ethyl-N-pyrrolidin-1-yl | N(CH$_3$)-phenyl | C$_{30}$H$_{42}$N$_6$O$_5$S$_2$ | 630.8 | 631.3 | |
| 38 | NH-benzyl | NH-ethyl-N(CH$_3$)$_2$ | N(CH$_3$)-phenyl | C$_{31}$H$_{37}$N$_5$O$_4$S$_2$ | 607.8 | 608.2 | |
| 39 | NH-ethyl-N(ethyl)$_2$ | NH-ethyl-N(CH$_3$)$_2$ | N(CH$_3$)-phenyl | C$_{30}$H$_{44}$N$_6$O$_4$S$_2$ | 616.8 | 617.3 | |
| 40 | NH-propyl-O—CH$_3$ | NH-ethyl-N-pyrrolidin-1-yl | N(CH$_3$)-phenyl | C$_{30}$H$_{41}$N$_5$O$_5$S$_2$ | 615.8 | 616.3 | |
| 41 | N-piperidinyl | N(ethyl)-ethyl-N(CH$_3$)$_2$ | N(CH$_3$)-phenyl | C$_{31}$H$_{43}$N$_5$O$_4$S$_2$ | 613.8 | 614.3 | |
| 42 | NH-ethyl-N-pyrrolidin-1-yl | NH-ethyl-N-pyrrolidin-1-yl | N(CH$_3$)-phenyl | C$_{32}$H$_{46}$N$_6$O$_4$S$_2$ | 642.9 | 643.3 | |
| 43 | NH-benzyl | NH-ethyl-N-pyrrolidin-1-yl | N(CH$_3$)-phenyl | C$_{33}$H$_{39}$N$_5$O$_4$S$_2$ | 633.8 | 634.3 | |
| 44 | N-piperidinyl | NH-ethyl-N-pyrrolidin-1-yl | N(CH$_3$)-phenyl | C$_{31}$H$_{41}$N$_5$O$_4$S$_2$ | 611.8 | 612.3 | |
| 45 | NH-ethyl-morpholin-4-yl | NH-ethyl-N-pyrrolidin-1-yl | N(CH$_3$)-phenyl | C$_{32}$H$_{44}$N$_6$O$_5$S$_2$ | 656.9 | 657.3 | |
| 46 | NH—CH$_2$-pyrid-2-yl | piperazin-1-yl | N(CH$_3$)-phenyl | C$_{30}$H$_{34}$N$_6$O$_4$S$_2$ | 606.8 | 607.3 | 89 |
| 47 | NH—CH$_2$-cyclohexyl | 4-N(CH$_3$)-piperazin-1-yl | NH-piperidin-4-yl-(1-N-ethyl-phenyl) | C$_{44}$H$_{65}$N$_7$O$_4$S$_2$ | 820.2 | | 175 |
| 48 | NH-benzyl | 4-N(CH$_3$)-piperazin-1-yl | NH-piperidin-4-yl-(1-N-ethyl-phenyl) | C$_{44}$H$_{59}$N$_7$O$_4$S$_2$ | 814.1 | | 111 (decomp.) |
| 49 | NH-ethyl-phenyl | 4-N(CH$_3$)-piperazin-1-yl | NH-piperidin-4-yl-(1-N-ethyl-phenyl) | C$_{45}$H$_{61}$N$_7$O$_4$S$_2$ | 828.2 | | 84 (decomp.) |
| 50 | NH-propyl-phenyl | 4-N(CH$_3$)-piperazin-1-yl | NH-piperidin-4-yl-(1-N-ethyl-phenyl) | C$_{46}$H$_{63}$N$_7$O$_4$S$_2$ | 842.2 | | 118 |
| 51 | Piperidin-1-yl | N(ethyl)-ethyl-N(CH$_3$)$_2$ | NH-ethyl-N(ethyl)$_2$ | C$_{29}$H$_{57}$N$_7$O$_4$S$_2$ | 631.9 | 632.4 | |
| 52 | NH-ethyl-phenyl | NH—CH(CH$_3$)-propyl-N(ethyl)$_2$ | piperidin-1-yl | C$_{33}$H$_{53}$N$_5$O$_4$S$_2$ | 647.9 | 648.4 | |
| 53 | NH-ethyl-thien-2-yl | piperazin-1-yl-4-ethyl-OH | piperidin-1-yl | C$_{28}$H$_{43}$N$_5$O$_5$S$_3$ | 625.9 | 626.3 | |
| 54 | NH-ethyl-thien-2-yl | NH—CH(CH$_3$)—(CH$_2$)$_3$-N(ethyl)$_2$ | piperidin-1-yl | C$_{31}$H$_{51}$N$_5$O$_4$S$_3$ | 654.0 | 654.3 | |
| 55 | NH-ethyl-N(CH$_3$)$_2$ | NH-ethyl-N(ethyl)$_2$ | NH-phenyl | C$_{28}$H$_{40}$N$_6$O$_4$S$_2$ | 588.8 | 589.3 | |
| 56 | NH-ethyl-phenyl | NH-ethyl-N(ethyl)$_2$ | NH-ethyl-N(ethyl)$_2$ | C$_{30}$H$_{53}$N$_7$O$_4$S$_2$ | 639.9 | 640.4 | |

TABLE 1-continued

Example I

| Ex. | R1 | R2 | X | Molecular formula | MW | MS (M + H⁺) | Mp (° C.) |
|---|---|---|---|---|---|---|---|
| 57 | N(ethyl)-ethyl-N(CH₃)₂ | 4-N(CH₃)-piperazin-1-yl | NH-ethyl-thien-2-yl | $C_{29}H_{44}N_6O_4S_4$ | 668.2 | 669.2 | |
| 58 | NH-benzyl | N-ethyl-N-pyrrolidinyl | N(ethyl)-ethyl-N(CH₃)₂ | $C_{31}H_{53}N_7O_4S_2$ | 651.9 | 652.3 | |
| 59 | N(CH₃)-benzyl | NH-ethyl-N-pyrrolidinyl | N(ethyl)-ethyl-N(CH₃)₂ | $C_{32}H_{55}N_7O_4S_2$ | 666.0 | 666.3 | |
| 60 | NH-benzyl | 4-N(CH₃)-piperazin-1-yl | N(ethyl)-ethyl-N(CH₃)₂ | $C_{30}H_{51}N_7O_4S_2$ | 637.9 | 638.3 | |
| 61 | N(CH₃)-benzyl | 4-N(CH₃)-piperazin-1-yl | N(ethyl)-ethyl-N(CH₃)₂ | $C_{31}H_{53}N_7O_4S_2$ | 651.9 | 652.3 | |
| 62 | NH-ethyl-phenyl | NH-ethyl-N-pyrrolidinyl | N(ethyl)-ethyl-N(CH₃)₂ | $C_{32}H_{55}N_7O_4S_2$ | 666.0 | 666.3 | |
| 63 | N(CH₃)-benzyl | NH-ethyl-N-pyrrolidinyl | NH—CH₂-cyclopropyl | $C_{28}H_{41}N_5O_4S_2$ | 575.8 | 576.3 | |
| 64 | Piperazin-1-yl-4-phenyl | N(ethyl)-ethyl-N(CH₃)₂ | piperidin-1-yl | $C_{32}H_{50}N_6O_4S_2$ | 646.9 | 647.3 | 116–118 |
| 65 | NH-piperidin-4-yl-N-benzyl | N(ethyl)-ethyl-N(CH₃)₂ | piperidin-1-yl | $C_{34}H_{54}N_6O_4S_2$ | 675.0 | 675.4 | |
| 66 | NH-ethyl-phenyl-3,4-(OCH₃)₂ | N(ethyl)-ethyl-N(CH₃)₂ | piperidin-1-yl | $C_{32}H_{51}N_5O_6S_2$ | 665.9 | 666.3 | |
| 67 | NH-ethyl-phenyl-4-Cl | N(ethyl)-ethyl-N(CH₃)₂ | piperidin-1-yl | $C_{30}H_{46}C_1N_5O_4S_2$ | 640.3 | 640.3 | |
| 68 | NH-ethyl-phenyl-4-NH₂ | N(ethyl)-ethyl-N(CH₃)₂ | piperidin-1-yl | $C_{30}H_{48}N_6O_4S_2$ | 620.9 | 621.3 | |
| 69 | NH-propyl-phenyl | N(ethyl)-ethyl-N(CH₃)₂ | piperidin-1-yl | $C_{31}H_{49}N_5O_4S_2$ | 619.9 | 620.3 | |
| 70 | NH-butyl-phenyl | N(ethyl)-ethyl-N(CH₃)₂ | piperidin-1-yl | $C_{32}H_{51}N_5O_4S_2$ | 633.9 | 634.3 | |
| 71 | N(CH₃)-ethyl-phenyl | N(ethyl)-ethyl-N(CH₃)₂ | piperidin-1-yl | $C_{31}H_{49}N_5O_4S_2$ | 619.9 | 620.3 | |
| 72 | Piperazin-1-yl-4-ethyl-phenyl | N(ethyl)-ethyl-N(CH₃)₂ | piperidin-1-yl | $C_{34}H_{54}N_6O_4S_2$ | 675.0 | 675.4 | |
| 73 | NH—CH₂-3,5-(CH₃)₂-phenyl | N(ethyl)-ethyl-N(CH₃)₂ | piperidin-1-yl | $C_{31}H_{49}N_5O_4S_2$ | 619.9 | 620.3 | |
| 74 | NH-ethyl-3-CF₃-phenyl | N(ethyl)-ethyl-N(CH₃)₂ | piperidin-1-yl | $C_{31}H_{46}F_3N_5O_4S_2$ | 673.9 | 674.3 | |
| 75 | NH-ethyl-O-phenyl | N(ethyl)-ethyl-N(CH₃)₂ | piperidin-1-yl | $C_{30}H_{47}N_5O_5S_2$ | 621.9 | 622.3 | |
| 76 | NH-ethyl-3,4-Cl₂-phenyl | N(ethyl)-ethyl-N(CH₃)₂ | piperidin-1-yl | $C_{30}H_{45}C_{12}N_5O_4S_2$ | 674.8 | 674.2 | |
| 77 | Piperazin-1-yl-4-phenyl | NH-ethyl-N-pyrrolidinyl | piperidin-1-yl | $C_{32}H_{48}N_6O_4S_2$ | 644.9 | 645.3 | |
| 78 | Piperidin-1-yl-4-phenyl | NH-ethyl-N-pyrrolidinyl | piperidin-1-yl | $C_{33}H_{49}N_5O_4S_2$ | 643.9 | 644.3 | |
| 79 | Piperidin-1-yl-4-benzyl | NH-ethyl-N-pyrrolidinyl | piperidin-1-yl | $C_{34}H_{51}N_5O_4S_2$ | 657.9 | 658.3 | |
| 80 | NH-ethyl-3,4(OCH₃)₂-phenyl | NH-ethyl-N-pyrrolidinyl | piperidin-1-yl | $C_{32}H_{49}N_5O_6S_2$ | 663.9 | 664.3 | |
| 81 | NH-propyl-phenyl | NH-ethyl-N-pyrrolidinyl | piperidin-1-yl | $C_{31}H_{47}N_5O_4S_2$ | 617.9 | 618.3 | |
| 82 | NH-butyl-phenyl | NH-ethyl-N-pyrrolidinyl | piperidin-1-yl | $C_{32}H_{49}N_5O_4S_2$ | 631.9 | 632.3 | |
| 83 | Piperazin-1-yl-4-ethyl-phenyl | NH-ethyl-N-pyrrolidinyl | piperidin-1-yl | $C_{34}H_{52}N_6O_4S_2$ | 673.0 | 673.4 | |
| 84 | NH—CH₂-(3-Cl-phenyl) | NH-ethyl-N-pyrrolidinyl | piperidin-1-yl | $C_{29}H_{42}C_1N_5O_4S_2$ | 624.3 | 624.2 | |
| 85 | NH-ethyl-O-phenyl | NH-ethyl-N-pyrrolidinyl | piperidin-1-yl | $C_{30}H_{45}N_5O_5S_2$ | 619.8 | 620.3 | |
| 86 | Piperazin-1-yl-4-CH₃ | NH-ethyl-N(ethyl)₂ | NH-phenyl | $C_{29}H_{40}N_6O_4S_2$ | 600.8 | 601.3 | |
| 87 | N(CH₃)-benzyl | NH-ethyl-N(CH₃)₂ | NH-ethyl-N(ethyl)₂ | $C_{30}H_{53}N_7O_4S_2$ | 639.9 | 640.4 | |
| 88 | N(CH₃)-benzyl | piperazin-1-yl-4-CH₃ | NH-ethyl-N(ethyl)₂ | $C_{31}H_{53}N_7O_4S_2$ | 651.9 | 652.4 | |
| 89 | Piperazin-1-yl-4-phenyl | NH-ethyl-N(CH₃)₂ | piperidin-1-yl | $C_{30}H_{46}N_6O_4S_2$ | 618.9 | 619.3 | |
| 90 | Piperidin-1-yl-4-phenyl | NH-ethyl-N(CH₃)₂ | piperidin-1-yl | $C_{31}H_{47}N_5O_4S_2$ | 617.9 | 618.3 | |
| 91 | Piperidin-1-yl-4-benzyl | NH-ethyl-pyrrolidinyl | NH—(CH₂)₃—O—CH₃ | $C_{32}H_{51}N_5O_6S_2$ | 665.9 | 666.3 | |
| 92 | NH-ethyl-3,4-(OCH₃)₂-phenyl | N(ethyl)-ethyl-N(CH₃)₂ | NH-ethyl-thien-2-yl | $C_{34}H_{47}N_5O_6S_4$ | 750.0 | 750.2 | |
| 93 | Piperidin-1-yl-4-phenyl | N(ethyl)-ethyl-N(CH₃)₂ | NH-ethyl-thien-2-yl | $C_{35}H_{47}N_5O_4S_4$ | 730.1 | 730.3 | |
| 94 | Piperazin-1-yl-4-phenyl | N(ethyl)-ethyl-N(CH₃)₂ | NH-ethyl-thien-2-yl | $C_{34}H_{48}N_6O_4S_4$ | 731.0 | 731.3 | |
| 95 | NH—CH₂-naphth-1-yl | NH-ethyl-N-pyrrolidinyl | NH-ethyl-thien-2-yl | $C_{35}H_{41}N_5O_4S_4$ | 724.0 | 724.2 | |
| 96 | Piperazin-1-yl-4-phenyl | N(ethyl)-ethyl-N(CH₃)₂ | NH-propyl-O—CH₃ | $C_{30}H_{50}N_6O_6S_2$ | 654.9 | 655.3 | |
| 97 | NH-(4-t-butyl)-benzyl | NH-ethyl-N-pyrrolidinyl | NH-ethyl-thien-2-yl | $C_{35}H_{47}N_5O_4S_4$ | 730.1 | 730.3 | |
| 98 | NH-(3,4-Cl₂)-benzyl | NH-ethyl-N(CH₃)₂ | Piperidin-1-yl | $C_{27}H_{39}C_{12}N_5O_4S_2$ | 632.7 | 632.2 | |
| 99 | NH-(3-Cl)-benzyl | NH-ethyl-N(CH₃)₂ | Piperidin-1-yl | $C_{27}H_{40}C_1N_5O_4S_2$ | 598.2 | 598.2 | |
| 100 | NH-(4-t-butyl)-benzyl | NH-ethyl-N(CH₃)₂ | Piperidin-1-yl | $C_{31}H_{49}N_5O_4S_2$ | 619.8 | 620.3 | |
| 101 | NH-ethyl-O-phenyl | NH-ethyl-N(CH₃)₂ | Piperidin-1-yl | $C_{28}H_{43}N_5O_5S_2$ | 593.8 | 594.3 | |
| 102 | Piperazin-1-yl-4-phenyl | NH-ethyl-N-pyrrolidinyl | NH—(CH₂)₃—O—CH₃ | $C_{30}H_{48}N_6O_6S_2$ | 652.9 | 653.3 | |
| 103 | NH-(4-t-butyl)-benzyl | NH-ethyl-N-pyrrolidinyl | NH—(CH₂)₃—O—CH₃ | $C_{31}H_{51}N_5O_6S_2$ | 653.9 | 654.3 | |
| 104 | Piperazin-1-yl-4-phenyl | NH-ethyl-N(CH₃)₂ | NH—(CH₂)₃—O—CH₃ | $C_{28}H_{46}N_6O_6S_2$ | 626.8 | 627.3 | |
| 105 | NH-(4-t-butyl)-benzyl | NH-ethyl-N(CH₃)₂ | NH—(CH₂)₃—O—CH₃ | C29H49N5O6S2 | 627.9 | 628.3 | |
| 106 | Piperazin-1-yl-4-phenyl | 4-N(CH₃)-piperazin-1-yl | NH—(CH₂)₃—O—CH₃ | $C_{29}H_{46}N_6O_6S_2$ | 638.9 | 639.3 | |
| 107 | NH-(4-t-butyl)-benzyl | 4-N(CH₃)-piperazin-1-yl | NH—(CH₂)₃—O—CH₃ | $C_{30}H_{49}N_5O_6S_2$ | 639.9 | 640.3 | |
| 108 | 1,2,5,6-tetrahydro-pyridin-1-yl-(4-phenyl) | 4-N(CH₃)-piperazin-1-yl | N(CH₃)-phenyl | $C_{36}H_{41}N_5O_4S_2$ | 671.9 | 672.3 | |

Compounds of formula I are distinguished by beneficial effects on lipid metabolism, and they are suitable in particular as hypolipidemics. The compounds can be employed alone or in combination with other lipid-lowering agents. Such other lipid-lowering agents are mentioned, for example, in the *Rote Liste*, chapter 58. The compounds are suitable for the prophylaxis and, in particular, for the treatment of hyperlipidemia.

Arteriosclerosis is a complex disorder of the metabolic and circulatory systems. Elevated plasma LDL cholesterol is one of the main risk parameters for this disorder. In humans, LDL cholesterol is mostly removed from the blood circulation via the LDL receptor in the liver. A reduction in the plasma LDL cholesterol reduces the risk of arteriosclerosis and thus also the overall mortality. Compounds according to the invention are thus also suitable for the prophylaxis and for the treatment of Earteriosclerotic disorders.

The activity of the compounds was tested as follows:
1) In Vitro Determination of LDL Receptor Induction Using the Luciferase Assay LDL-receptor induction is determined using the luciferase assay as follows. A regulatory DNA fragment (4 kb) of the human LDL receptor gene containing the complete promoter region is coupled to the firefly luciferase reporter gene and stably transfixed into a Hep-G2 cell line. Cells from this line were seeded out on collagen-coated 96-well plates in MEM (minimum essential medium). After 24 hours in culture, the test substances, dissolved in DMSO, were added in final concentrations of 10 nM to 10 $\mu$M (final DMSO concentration=2%). The substances were incubated for 12–18 hours overnight (4 wells/conc. in each case), then D-luciferin was added as substrate for the luciferase, and the luminescence was measured. The measured luminescence as a percentage of the control (control=100%) incubated only with DMSO indicates the extent of the relative LDL receptor induction (Table 2).

Further details of the method are described in *Current Protocols in Molecular Biology*, F. M. Ausubel, R. Brent, R. E. Kingston, D. D. Moore, J. G. Seidman, J. A. Smith, and K. Struhl, eds., J. Wiley and Sons Inc., U.S.A.

TABLE 2

| LDL receptor induction by selected examples as % of the control | |
|---|---|
| Example | LDL receptor induction (% of control) |
| 1 | 195% (1.5 $\mu$M) |
| 2 | 227% (4 $\mu$M); 155% (1.5 $\mu$M) |
| 3 | 414% (1.5 $\mu$M); 184% (0.15 $\mu$M) |
| 5 | 240% (4 $\mu$M) |
| 6 | 299% (4 $\mu$M) |
| 8 | 190% (4 $\mu$M) |
| 9 | 402% (1.5 $\mu$M); 244% (0.15 $\mu$M) |
| 10 | 270% (4 $\mu$M); 144% (0.15 $\mu$M) |
| 12 | 244% (1.5 $\mu$M) |
| 15 | 243% (1.5 $\mu$M); 137% (0.15 $\mu$M) |
| 16 | 214% (1.5 $\mu$M) |
| 25 | 189% (1.5 $\mu$M); 168% (0.15 %) |
| 26 | 206% (1.5 $\mu$M); 146% (0.15 $\mu$M) |
| 46 | 223% (1.5 $\mu$M); 152% (0.15 $\mu$M) |
| 58 | 219% (4 $\mu$M); 196% (1.5 $\mu$M) |
| 61 | 190% (4 $\mu$M) |
| 65 | 314% (4 $\mu$M); 292% (1.5 $\mu$M); 177% (0.15 $\mu$M) |
| 70 | 238% (4 $\mu$M); 194% (0.15 $\mu$M) |
| 84 | 223% (4 $\mu$M); 199% (1.5 $\mu$M) |
| 92 | 233% (4 $\mu$M); 213% (1.5 $\mu$M) |
| 93 | 337% (4 $\mu$M); 293% (1.5 $\mu$M); 213% (0.15 $\mu$M) |
| 94 | 321% (4 $\mu$M); 194% (1.5 $\mu$M) |
| 95 | 301% (4 $\mu$M); 267% (1.5 $\mu$M); 198% (0.15 $\mu$M) |
| 96 | 326% (4 $\mu$M); 278% (1.5 $\mu$M); 138% (0.15 $\mu$M) |
| 98 | 285% (4 $\mu$M); 249% (1.5 $\mu$M) |
| 99 | 322% (4 $\mu$M); 247% (1.5 $\mu$M) |
| 102 | 298% (4 $\mu$M); 239% (1.5 $\mu$M) |
| 108 | 249% (4 $\mu$M); 191% (1.5 $\mu$M) |

In Vivo Determination of Reduction in LDL Cholesterol in the Hamster; Cholesterol-lowering Effect of LDL Receptor Inducers in Hyperlipemic Hamsters In this animal experiment, the effect of LDL receptor inducers after bolus adiminstration to hamsters on a lipid-rich diet was investigated.

The experimental animals used were male Syrian hamsters (Charles River) with an average body weight of 100 to 120 g at the start of adaption. The animals were divided into groups (n=6) on the basis of the body weight. Severe hyperlipidemia was induced by feeding with a diet supplemented with 15% butter and 3% cholesterol. The treatment started after preliminary feeding for 2 weeks. The test substances were administered orally by gavage once a day over a period of 10 days. The plasma lipid level was analyzed after 10 days.

Table 3 shows the relative changes in the lipid level in % compared with placebo-treated control animals.

TABLE 3

Relative change in the plasma lipid level in hyperlipemic hamsters after oral treatment for ten days (%)

| Group | Treatment (Exp. No./dose) | Total cholesterol | LDL cholesterol | Triglycerides |
|---|---|---|---|---|
| 1 | Control I | — | — | — |
| 2 | 95 20 mg/kg p.o. | −45 | −44 | −61 |
| 3 | 95 40 mg/kg p.o. | −50 | −49 | −73 |
| 4 | 98 20 mg/kg p.o. | −23 | −26 | −27 |
| 5 | 98 40 mg/kg p.o. | −46 | −44 | −68 |

The good lipid-lowering effect of compounds according to the invention is evident from the marked reduction in total cholesterol, LDL cholesterol, and triglycerides.

For detailed illustration of the preparation, one example (No. 64) is described precisely below.

EXAMPLE

N-Ethyl-N',N'-dimethyl-N-[5-(4-phenyl-piperazin-1-yl)-2,4-bis-(piperidine-1-sulfonyl)-phenyl]ethane-1,2-diamine (Table 1, Example 64)

2.63 g (5.1 mmol) of N-[5-chloro-2,4-bis-(piperidine-1-sulfonyl)-phenyl]-N-ethyl-N',N'-dimethylethane-1,2-diamine, prepared as described below, are dissolved in 12 ml of 4-phenylpiperazine, and the reaction mixture is stirred at 90° C. for 9 hours. Workup entails extraction with ethyl acetate/water, drying of the combined organic phases over sodium sulfate, and removing the extractant under reduced pressure in a rotary evaporator. This is followed by purification by chromatography on silica gel (40–63$\mu$, Merck Darmstadt; mobile phase=dichloromethane/methanol=20/1).

The reaction product, yield 1.43 g (44%), crystallizes from a diisopropyl ether/n-pentane solvent mixture in the form of pale yellow crystals of melting point 116 to 118° C.

$C_{32}H_{50}N_6O_4S_2$ (646.9); mass spectrum=647.3 (M+H$^+$).

Synthesis of N-[5-Chloro-2,4-bis-(piperidine-1-sulfonyl)-phenyl]-N-ethyl-N',N'-dimethylethane-1,2-diamine 11.2 g (25.3 mmol) of 4,6-dichloro-N,N-dipiperidylbenzene-1,3-disulfonamide (prepared as described below) are dissolved in 100 ml of ethanol, and 4.26 g of N,N-dimethyl-N'-ethylenediamine are added. The reaction mixture is heated to reflux in the solvent for 12 hours. It is then poured into 500 ml of ice-water and extracted three times with 100 ml of ethyl acetate each time. The organic phases are combined and dried with sodium sulfate, and the extract is removed under reduced pressure in a rotary evaporator, and then the product is purified by chromatography on silica gel (40–63μ, Merck Darmstadt; mobile phase=dichloromethane/ethylacetate=20/1).

Removal of the solvent results in 6.8 g of N-[5-chloro-2,4-bis-(piperidine-1-sulfonyl)-phenyl]-N-ethyl-N',N'-dimethylethane-1,2-diamine, yield 52% of theory, colorless oil.

$C_{22}H_{37}ClN_4O_4S_2$ (521.1), mass spectrum=521.2 (M+H⁺).

Synthesis of 4,6-Dichloro-N,N-dipiperidylbenzene-1,3-disulfonamide 20 g (58 mmol) of 4,6-dichlorobenzene-1,3-disulfonyl dichloride (prepared as described below) are dissolved in 175 ml of absolute tetrahydrofuran and, while cooling at 0° C. in ice, a mixture of 12.65 ml of piperidine, 16.1 ml of triethylamine, and 10 ml of tetrahydrofuran is added dropwise. The reaction temperature must not increase above room temperature during this. The mixture is then stirred at room temperature for one hour and filtered to remove the precipitate which has formed. The mother liquor is dried with sodium sulfate and concentrated under reduced pressure, and the product is purified by chromatography on silica gel (40–63μ, Merck Darmstadt; mobile phase=n-heptane/ethyl acetate=½).

18.2 g (71.1% of theory) of 4,6-dichloro-N,N-dipiperidylbenzene-1,3-disulfonamide of melting point 170° C. are obtained.

Synthesis of 4,6-Dichlorobenzene-1,3-disulfonyl Dichloride 80 g (0.54 mol) of 1,3-dichlorobenzene are dissolved in 645 g of chlorosulfonic acid and stirred at 125° C. for 5 hours. The mixture is then stirred at 23° C. for 8 hours. Then, 145.6 ml of thionyl chloride are added with cooling, and the mixture is stirred at 80° C. for 2 hours. The reaction mixture is then hydrolyzed by dropwise addition of 42 ml of water cautiously and with efficient cooling. The reaction solution is then added dropwise at 0° C. to about 3.5 l of ice/water mixture. This precipitates the reaction product as a colorless solid, which is then filtered off.

After drying, 179.2 g of 4,6-dichlorobenzene-1,3-disulfonyl dichloride (95% of theory) of melting point 104° C. are obtained; the product melts with decomposition.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A method of treating hyperlipidemia, comprising administering to a patient in need thereof an effective amount of at least one compound of formula I,

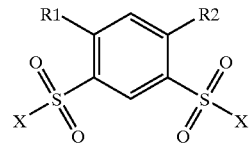

in which:

X, R1, and R2 are, independently of one another, NR6R7, pyrrolidinyl, piperidinyl, piperazinyl, morpholinyl, or tetrahydropyridinyl, in which each ring is optionally substituted by phenyl, $(C_1–C_6)$-alkyl-phenyl, $(C_1–C_6)$-alkyl, $(C_1–C_6)$-alkyl-OH, O-phenyl, S-phenyl, (CO)—$(C_1–C_6)$-alkyl, or (CO)-phenyl, where the phenyl substituent is unsubstituted or mono- or disubstituted by F, Cl, Br, OH, $CF_3$, CN, $OCF_3$, O—$(C_1–C_6)$-alkyl, S—$(C_1–C_6)$-alkyl, SO—$(C_1–C_6)$-alkyl, $SO_2$—$(C_1–C_6)$-alkyl, $(C_1–C_6)$-alkyl, $(C_3–C_6)$-cycloalkyl, COOH, COO$(C_1–C_6)$alkyl, COO$(C_3–C_6)$cycloalkyl, $CONH_2$, CONH$(C_1–C_6)$alkyl, CON[$(C_1–C_6)$alkyl]$_2$, CONH$(C_3–C_6)$cycloalkyl, $NH_2$, NH—CO—$(C_1–C_6)$-alkyl, or NH—CO-phenyl;

R6 and R7 are, independently of one another, H, $(C_1–C_6)$-alkyl, $(C_1–C_6)$-alkyl-O—$(C_1–C_6)$-alkyl, O—$(C_1–C_6)$-alkyl, $(C_3–C_6)$-cycloalkyl, CO—$(C_1–C_6)$-alkyl, $(C_1–C_6)$-alkyl-NH—C(O)—$(C_1–C_6)$-alkyl, $(C_1–C_6)$-alkyl-NH—$(C_1–C_6)$-alkyl, $(C_1–C_6)$-alkyl-N—[$(C_1–C_6)$-alkyl]$_2$, $(C_1–C_6)$-alkyl-O-phenyl, CHO, CO-phenyl, or $(CH_2)_n$—Ar, where n is the integer 0, 1, 2, 3, 4, 5, or 6, and Ar is chosen from phenyl, biphenylyl, 1- or 2-naphthyl, 1- or 2-tetrahydrofuranyl, 2-, 3-, or 4-pyridyl, 2- or 3-thienyl, 2- or 3-furyl, 2-, 4-, or 5-thiazolyl, 2-, 4-, or 5-oxazolyl, 1-pyrazolyl, 3-, 4-, or 5-isoxazolyl, $(C_3–C_6)$-cycloalkyl, piperidinyl, pyrrolidinyl, 2- or 3-pyrrolyl, 2- or 3-pyridazinyl, 2-, 4-, or 5-pyrimidinyl, 2-pyrazinyl, 2-(1,3,5-triazinyl), 2-, 3-, or 4-morpholinyl, 2- or 5-benzimidazolyl, 2-benzothiazolyl, 1,2,4-triazol-3-yl, 1,2,4-triazol-5-yl, tetrazol-5-yl, indol-3-yl, indol-5-yl, or N-methylimidazol-2-, -4-, or -5-yl, and Ar is optionally mono- or disubstituted by F, Cl, Br, OH, $CF_3$, $NO_2$, CN, $OCF_3$, O—$CH_2$—O, O—$(C_1–C_6)$-alkyl, S—$(C_1–C_6)$-alkyl, SO—$(C_1–C_6)$-alkyl, $SO_2$—$(C_1–C_6)$-alkyl, $(C_1–C_6)$-alkyl, $(C_3–C_6)$-cycloalkyl, COOH, COO$(C_1–C_6)$alkyl, COO$(C_3–C_6)$cycloalkyl, $CONH_2$, CONH$(C_1–C_6)$alkyl, CON[$(C_1–C_6)$alkyl]$_2$, CONH$(C_3–C_6)$cycloalkyl, $NH_2$, NH—CO—$(C_1–C_6)$-alkyl, NH—CO-phenyl, pyrrolidin-1-yl, morpholin-1-yl, piperidin-1-yl, piperazin-1-yl, 4-methyl-piperazin-1-yl, $(CH_2)_n$-phenyl, O—$(CH_2)_n$-phenyl, S—$(CH_2)_n$-phenyl, or $SO_2$—$(CH_2)_n$-phenyl, where n is the integer 0, 1, 2, or 3;

or a salt or ester thereof.

2. A method of treating hyperlipidemia, comprising administering to a patient in need thereof an effective amount of at least one compound of claim 1, in which:

R1 is NR6R7, pyrrolidinyl, piperidinyl, piperazinyl, or tetrahydropyridinyl, in which each ring is optionally substituted by phenyl, $(C_1–C_6)$-alkyl-phenyl, $(C_1–C_6)$-alkyl, $(C_1–C_6)$-alkyl-OH, O-phenyl, S-phenyl, (CO)—$(C_1–C_6)$-alkyl, or (CO)-phenyl, where the phenyl substituent is unsubstituted or mono- or disubstituted by F, Cl, Br, $CF_3$, CN, $OCF_3$, O—$(C_1–C_6)$-alkyl, S—$(C_1–C_6)$-alkyl, $(C_1–C_6)$-alkyl, $(C_3–C_6)$-cycloalkyl, COOH, COO$(C_1–C_6)$-alkyl, COO$(C_3–C_6)$cycloalkyl, CONH$_2$, CONH(C$_1$–C$_6$)alkyl, CON[(C$_1$–C$_6$)alkyl]$_2$, NH$_2$, NH—CO—(C$_1$–C$_6$)-alkyl, or NH—CO-phenyl;

R6 and R7 are, independently of one another, H, (C$_1$–C$_6$)-alkyl, (C$_1$–C$_6$)-alkyl-O—(C$_1$–C$_6$)-alkyl, (C$_3$–C$_6$)-cycloalkyl, CO—(C$_1$–C$_6$)-alkyl, (C$_1$–C$_6$)-alkyl-NH—C(O)—(C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, or (CH$_2$)$_n$—Ar, where n is the integer 0, 1, 2, 3, 4, 5, or 6, and Ar is chosen from phenyl, biphenylyl, 1- or 2-naphthyl, 2-, 3-, or 4-pyridyl, 2- or 3-thienyl, 2-, 4-, or 5-thiazolyl, 2-, 4-, or 5-oxazolyl, 3- or 5-isoxazolyl, (C$_3$–C$_6$)-cycloalkyl, piperidinyl, pyrrolidinyl, 2-, 4-, or 5-pyrimidinyl, 2-, 3-, or 4-morpholinyl, 2- or 5-benzimidazolyl, 2-benzothiazolyl, indol-3-yl, or indol-5-yl, and Ar is optionally mono- or disubstituted by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$)alkyl, NH$_2$, NH—CO-phenyl, (CH$_2$)$_n$-phenyl, O—(CH$_2$)$_n$-phenyl, or S—(CH$_2$)$_n$-phenyl, where n is the integer 0, 1, 2, or 3;

R2 is NR8R9 or piperazinyl, in which piperazinyl is optionally substituted by (C$_1$–C$_6$)-alkyl-phenyl, (C$_1$–C$_6$)-alkyl, (C$_1$–C$_6$)-alkyl-OH, O-phenyl, S-phenyl, (CO)—(C$_1$–C$_6$)-alkyl, or (CO)-phenyl;

R8 and R9 are, independently of one another, H, (C$_1$–C$_6$)-alkyl, (C$_3$–C$_6$)-cycloalkyl, CO—(C$_1$–C$_6$)-alkyl, (C$_1$–C$_6$)-alkyl-NH—(C$_1$–C$_6$)-alkyl, ($_1$–C$_6$)-alkyl-N—[(C$_1$–C$_6$)-alkyl]$_2$, or (CH$_2$)$_n$—Ar, where n is the integer 0, 1, 2, 3, 4, 5, or 6, and Ar is chosen from phenyl, 2-, 3-, or 4-pyridyl, piperidinyl, pyrrolidinyl, or morpholinyl;

X is NR10R11, pyrrolidinyl, piperidinyl, piperazinyl, or morpholinyl, in which each ring is optionally substituted by phenyl, (C$_1$–C$_6$)alkyl-phenyl, (C$_1$–C$_6$)-alkyl, (C$_1$–C$_6$)-alkyl-OH, O-phenyl, S-phenyl, (CO)—(C$_1$–C$_6$)-alkyl, or (CO)-phenyl, where the phenyl substituent is unsubstituted or mono- or disubstituted by F, Cl, Br, CF$_3$, CN, OCF$_3$, O—(C$_1$–C$_6$)-alkyl, (C$_1$–C$_6$)-alkyl, (C$_3$–C$_6$)-cycloalkyl, COOH, COO(C$_1$–C$_6$)-alkyl, COO(C$_3$–C$_6$)cycloalkyl, CONH$_2$, CONH(C$_1$–C$_6$)alkyl, CON[(C$_1$–C$_6$)alkyl]$_2$, NH$_2$, NH—CO—(C$_1$–C$_6$)-alkyl, or NH—CO-phenyl;

R10 and R11 are, independently of one another, H, (C$_1$–C$_6$)-alkyl, (C$_1$–C$_6$)-alkyl-O—(C$_1$–C$_6$)-alkyl, (C$_3$–C$_6$)-cycloalkyl, CO—(C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, CO-phenyl, or (CH$_2$)$_n$—Ar, where n is the integer 0, 1, 2, 3, 4, 5, or 6, and Ar is chosen from phenyl, biphenylyl, 1- or 2-naphthyl, 1- or 2-tetrahydrofuranyl, 2-, 3-, or 4-pyridyl, 2- or 3-thienyl, 2- or 3-furyl, 2-, 4-, or 5-thiazolyl, 2-, 4-, or 5-oxazolyl, 3- or 5-isoxazolyl, piperidinyl, pyrrolidinyl, 2-, 4-, or 5-pyrimidinyl, 2-, 3-, or 4-morpholinyl, or 2-benzothiazolyl, and Ar is optionally mono- or disubstituted by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, CONH$_2$, CONH(C$_1$–C$_6$)alkyl, CON[(C$_1$–C$_6$)alkyl]$_2$, NH—CO—(C$_1$–C$_6$)-alkyl, NH—CO-phenyl, or (CH$_2$)$_n$-phenyl, where n is the integer 0, 1, 2, or 3;

or a salt or ester thereof.

3. A method of treating hyperlipidemia, comprising administering to a patient in need thereof an effective amount of at least one compound of claim 1, in which:

R1 is NR6R7, piperidinyl, piperazinyl, or tetrahydropyridinyl, in which each ring is optionally substituted by phenyl or (C$_1$–C$_6$)-alkyl-phenyl;

R6 and R7 are, independently of one another, H, (C$_1$–C$_6$)-alkyl, (C$_1$–C$_6$)-alkyl-O—(C$_1$–C$_6$)-alkyl, (C$_3$–C$_6$)-cycloalkyl, (C$_1$–C$_6$)-alkyl-NH—C(O)—(C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, or (CH$_2$)$_n$—Ar, where n is the integer 0, 1, 2, 3, 4, 5, or 6, and Ar is chosen from phenyl, 1- or 2-naphthyl, 2-, 3-, or 4-pyridyl, (C$_3$–C$_6$)-cycloalkyl, piperidinyl, pyrrolidinyl, 2-, 4-, or 5-pyrimidinyl, 2-, 3-, or 4-morpholinyl, and Ar is optionally mono- or disubstituted by F, Cl, Br, OH, CF$_3$, NO$_2$, CN, OCF$_3$, O—(C$_1$–C$_6$)-alkyl, (C$_1$–C$_6$)-alkyl, or NH$_2$;

R2 is NR8R9 or piperazinyl, in which piperazinyl is optionally substituted by (C$_1$–C$_6$)-alkyl;

R8 and R9 are, independently of one another, H, (C$_1$–C$_6$)-alkyl, (C$_3$–C$_6$)-cycloalkyl, CO—(C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, or (CH$_2$)$_n$—Ar, where n is the integer 0, 1, 2, 3, 4, 5, or 6, and Ar is chosen from phenyl, 2-, 3-, or 4-pyridyl, piperidinyl, pyrrolidinyl, or morpholinyl;

X is NR10R11, pyrrolidinyl, piperidinyl, or morpholinyl, in which each ring is optionally substituted by phenyl or (C$_1$–C$_6$)-alkyl-phenyl;

R10 and R11 are, independently of one another, H, (C$_1$–C$_6$)-alkyl, (C$_1$–C$_6$)-alkyl-O-(C$_1$–C$_6$)-alkyl, (C$_3$–C$_6$)-cycloalkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, or (CH$_2$)$_n$—Ar, where n is the integer 0,1, 2, 3, 4, 5, or 6 and Ar is chosen from phenyl or 2- or 3-thienyl;

or a salt or ester thereof.

4. The method of claim 1, wherein 0.3 to 100 mg/kg/day of at least one compound of claim 1 is administered.

5. The method of claim 1, wherein 0.3 to 50 mg/kg/day of at least one compound of claim 1 is administered.

6. The method of claim 1, wherein 0.3 to 10 mg/kg/day of at least one compound of claim 1 is administered.

7. The method of claim 1, wherein 0.3 to 1 mg/kg of at least one compound of claim 1 is administered intravenously.

8. A method of treating hyperlipidemia, comprising administering to a patient in need thereof an effective amount of at least one compound of claim 1 and at least one lipid-lowering agent.

\* \* \* \* \*

UNITED STATES PATENT AND TRADEMARK OFFICE
CERTIFICATE OF CORRECTION

PATENT NO. : 6,632,838 B1
DATED : October 14, 2003
INVENTOR(S) : Kirsch et al.

It is certified that error appears in the above-identified patent and that said Letters Patent is hereby corrected as shown below:

<u>Title page,</u>
Item [73], Assignee, "Frankfrut" should read -- Frankfurt --.

<u>Column 17,</u>
Lines 29-30, "$(_1\text{-}C_6)$-alkyl-N-$[(C_1\text{-}C_6)$-alkyl$]_2$," should read
-- $(C_1\text{-}C_6)$-alkyl-N-$[(C_1\text{-}C_6)$-alkyl$]_2$, --.

Signed and Sealed this

Second Day of March, 2004

JON W. DUDAS
*Acting Director of the United States Patent and Trademark Office*